United States Patent
Wang et al.

(10) Patent No.: US 7,754,765 B2
(45) Date of Patent: Jul. 13, 2010

(54) COPPER CHELATORS FOR TREATING OCULAR INFLAMMATION

(75) Inventors: Xuefeng Wang, Vancouver (CA); Jing Z. Cui, Vancouver (CA); Joanne A. Matsubara, Vancouver (CA)

(73) Assignee: Radical Vision Therapeutics Inc, Vancouver, B.C. (CA)

( * ) Notice: Subject to any disclaimer, the term of this patent is extended or adjusted under 35 U.S.C. 154(b) by 399 days.

(21) Appl. No.: 10/452,804

(22) Filed: May 30, 2003

(65) Prior Publication Data
US 2003/0232799 A1 Dec. 18, 2003

Related U.S. Application Data

(63) Continuation-in-part of application No. 10/005,465, filed on Dec. 3, 2001, now abandoned, and a continuation-in-part of application No. PCT/CA01/01735, filed on Nov. 30, 2001.

(60) Provisional application No. 60/250,164, filed on Dec. 1, 2000.

(51) Int. Cl.
A61K 31/13 (2006.01)
A61K 31/205 (2006.01)

(52) U.S. Cl. .......... 514/554; 514/674; 514/912

(58) Field of Classification Search .......... 514/554, 514/674, 912
See application file for complete search history.

(56) References Cited

U.S. PATENT DOCUMENTS

| | | | |
|---|---|---|---|
| 4,323,558 A * | 4/1982 | Nelson | 424/702 |
| 4,522,811 A | 6/1985 | Eppstein | |
| 4,904,698 A | 2/1990 | Adkins, Jr. et al. | 514/642 |
| 5,171,749 A | 12/1992 | Levy | |
| 5,420,120 A * | 5/1995 | Boltralik | 514/172 |
| 5,798,349 A | 8/1998 | Levy | |
| 5,834,457 A | 11/1998 | Bredesen et al. | 514/188 |
| 5,910,513 A * | 6/1999 | Galey | 514/649 |

OTHER PUBLICATIONS

Brown L. and Langer R., Annual Review of Medicine, (1988) 39:221-229.
Ciulla T.A., et al. Surv. Opthalmol., (1998) 43(2):132-146.
Jackson et al. Faseb J., (1997) 11(6):457-65.
Jeremy J.Y. et al., J. Drug Dev. Clin. Pract. (1995), 7:119-126.
Majno G., Am. J. Pathol., (1998) 153(4):1035-9.
McGahan M.C. et al. Agents and Actions(1991), 34(3/4):405-409.
Milanino R. et al., Int. J. Tiss. Reac. (1985), VII(6):469-474.
Schmidt-Erfurth U. et al. Arch. Opthalmol. (1999), 117(9):1177-87.
Sorenson J.R.J. In: Milanino R. et al. editors. Copper and Zinc in Inflammation. Dordrecht: Kluwer Academic Publishers (1989):69-84.

(Continued)

*Primary Examiner*—Zohreh A Fay
(74) *Attorney, Agent, or Firm*—Bret E. Field; Bozicevic, Field & Francis LLP

(57) ABSTRACT

In various aspects, the invention provides methods for treating ocular inflammation using copper chelating compounds, such as compounds other than D-penicillamine. In some embodiments, such compounds may be polyamines, such as triethylenetetramine or tetraethylenepentamine. For example, the present invention provides methods for treating inflammation secondary to ocular laser therapy.

27 Claims, 4 Drawing Sheets

OTHER PUBLICATIONS

Krejci, L., "A new neutralizing agent diethylenetriamine (DETA) in the treatment of acid burns of the eyes. II. Clinical Part!", *Ceskoslovenska Oftalmologie*, vol. 23, No. 4, Jul. 1967, pp. 283-287.

Diethylenetriamine as first aid in eye burns with phenol and aldehydes, *Ceskoslovenska Oftalmologie*, vol. 24, No. 2, Mar. 1968, pp. 132-134.

McGahn, M.C. et al., "Copper Depletion and D Penicillamine Treatment Alter Some Parameters of the Ocular Inflammatory Response", *Investigative Ophthalmology & Visual Science*, vol. 29, no. Abstr. Issue, 1988, p. 287.

Moreau, J.M. et al., "Phospholipase A(2) in rabbit tears: a host defense against Staphyloccus aureus", *Investigative Ophthalmology & Visual Science*, vol. 42, No. 10, Sep. 2001, pp. 2347-2354.

McGahn, M.C. et al., "The pathophysiology of the ocular microenvironment. II. Copper-induced ocular inflammation and hypotony", *Experimental Eye Research*, vol. 42, No. 6, Jun. 1986, pp. 595-605.

Bolos, C.A. et al., "Structure-activity relationship for some diamine, triamine and Schiff base derivatives and their copper(II) complexes", *Metal-Based Drugs*, vol. 5, No. 6, 1998, pp. 323-332.

Al-Abdullah Ismail, H. et al., "Neogenesis of pancreatic endocrine cells in copper-deprived rat models", *Pancreas*, vol. 21, No. 1, Jul. 2000, pp. 63-68.

Patent Abstracts of Japan, vol. 2000, No. 10, Nov. 17, 2000, & JP 2000 204037 A (Tsumura & Amp; Co; Sakoda Saburo), Jul. 25, 2000, Abstract.

\* cited by examiner

COPPER CHELATORS FOR TREATING OCULAR INFLAMMATION

FIELD OF THE INVENTION

In one aspect, the present invention relates to therapeutic uses of organic compounds, including nitrogen-containing compounds such as polyamines, as well as therapeutic compositions containing such compounds, such as ophthalmological medicaments.

BACKGROUND OF THE INVENTION

Copper chelation therapy is most often associated with Wilson's disease, an autosomal recessive disorder of copper metabolism. In this disorder, the excretion of copper into the bile appears to be defective, and reduced hepatic incorporation of copper into ceruloplasmin occurs, leading to an accumulation of copper in plasma and body tissues. Wilson's disease often leads to hepatic and/or neurologic dysfunction, and premature osteoarthritis. Two commonly used copper chelators for the treatment of Wilson's disease are D-penicillamine (DPA) and triethylenetetramine (trientine or TRIEN).

Patients with rheumatoid arthritis show elevated levels of copper and copper-binding protein, ceruloplasmin, in serum and in synovial fluid, and copper chelation therapy has been suggested for patients with rheumatoid arthritis and other inflammatory diseases (Milanino R. et al., Copper Metabolism in the Acute Inflammatory Process and its Possible Significance for a Novel Approach to the therapy of Inflammation. Int. J. Tiss. Reac. (1985) VII(6):469-474). Complexing drugs with copper has also been suggested to improve the efficacy of anti-inflammatory medications (Sorenson J. R. J. In: Milanino R. et al. editors. Copper and zinc in inflammation. Dordrecht: Kluwer Academic Publishers (1989):69-84). However, the various effects of copper on the inflammatory response in different tissues have not yet been thoroughly elucidated (Jeremy J. Y. et al. Copper Chelators Inhibit Platelet Thromboxane $A_2$ Synthesis and Lipoxygenase Activity, in vitro. J. Drug Dev. Clin. Pract. (1995) 7:119-126). For example, it has been suggested that copper depletion, including depletion by treatment with copper chelators, may reduce levels of ceruloplasmin and thereby exacerbate some measures of occular inflammation (McGahan M. C. et al. Effects of Copper Depletion and D-penicillamine Treatment of the Ocular Inflammatory Response. Agents and Actions (1991) 34(3):405-509). Choroidal neovascularization (CNV) due to age-related macular degeneration (AMD) is a leading cause of severe vision loss in elderly people. Therapies for CNV have included laser photocoagulation and photodynamic therapy (PDT, such as methods disclosed in, but not limited to, U.S. Pat. No. 5,171,749 issued Dec. 15, 1992, incorporated herein by reference). The former uses a thermal laser to destroy capillaries, with nonselective tissue damage. The latter is a relatively new therapy employing a photosensitizer, which is activated by a non-thermal laser. The therapeutic effect of PDT is generally thought to result at least partially from the formation of reactive oxygen species (ROS) or free radicals, which are cytotoxic.

Laser therapy, however, can also generate an inflammatory response, which can result in damage of normal tissue and recurrence of neovascularization, compromising therapeutic efficacy. It has been suggested that an inflammatory response, secondary to laser treatment, may play a role in inducing pathological side effects (Schmidt-Erfurth U., et al., Photodynamic therapy with verteporfin for choroidal neovascularization caused by age-related macular degeneration: results of retreatments in a phase 1 and 2 study. Arch Ophthalmol, (1999) 117(9): 1177-87; Ciulla T. A., et al., Age-related macular degeneration: a review of experimental treatments. Surv Ophthalmol, (1998) 43(2):134-46; Jackson J. R., et al., The codependence of angiogenesis and chronic inflammation. Faseb J, (1997) 11(6):457-65; Majno G., Chronic inflammation: links with angiogenesis and wound healing. Am J Pathol, (1998) 153(4):1035-9).

SUMMARY OF THE INVENTION

In various aspects, the invention provides methods for treating ocular inflammation using copper chelating compounds other than D-penicillamine. For example, the present invention provides methods for treating inflammation secondary to laser therapy of CNV. Laser therapy may for example include PDT and laser photocoagulation for the treatment of CNV, as well as laser therapies used to treat other eye diseases.

The invention provides the unexpected and surprising result that administrating copper chelating compounds to an animal or human patient has an ocular anti-inflammatory effect. Copper chelating compounds of the invention may include polyamines, such as triethylenetetramine (CAS Registry No. 112-24-3; synonyms: TRIEN; TETA; N,N'-bis(2-aminoethyl)-ethylenediamine; N,N'-bis(2-aminoethyl)-1,2-ethanediamine; 1,8-diamino-3,6-diazaoctane; 3,6-diazaoctane-1,8-diamine; 1,4,7,10-tetraazadecane; tecza; trien; trientine; N,N'-bis(aminoethyl)ethylenediamine; DEH 24; N,N'-bis(2-aminoethyl)ethanediamine; triethylenetetraamine; formula $C_6H_{18}N_4$) or tetraethylenepentamine (CAS Registry No. 112-57-2; synonyms: TETREN; 1,4,7,10,13-pentaazatridecane; N-(2-aminoethyl)-N'-(2-((2-aminoethyl)amino)ethyl)-1,2-ethanediamine; 1,11-diamino-3,6,9-triazaundecane; D.E.H. 26; 3,6,9-triaza-1,11-undecanediamine; 3,6,9-triazaundecamethylenediamine; 3,6,9-triazaundecane-1,11-diamine; formula $C_8H_{23}N_5$). In some formulations, copper chelating compounds containing sulfhydryl groups, such as D-penicillamine, may not be effective.

In alternative embodiments, copper chelating therapy may be used to inhibit ocular inflammatory responses caused by trauma, exposure to UV light, chemical stimuli and toxins. Thus, the present invention also provides a method for treating inflammation secondary to other pathological conditions, such as trauma, UV, chemical stimuli, and toxins.

DETAILED DESCRIPTION

Figure 1:
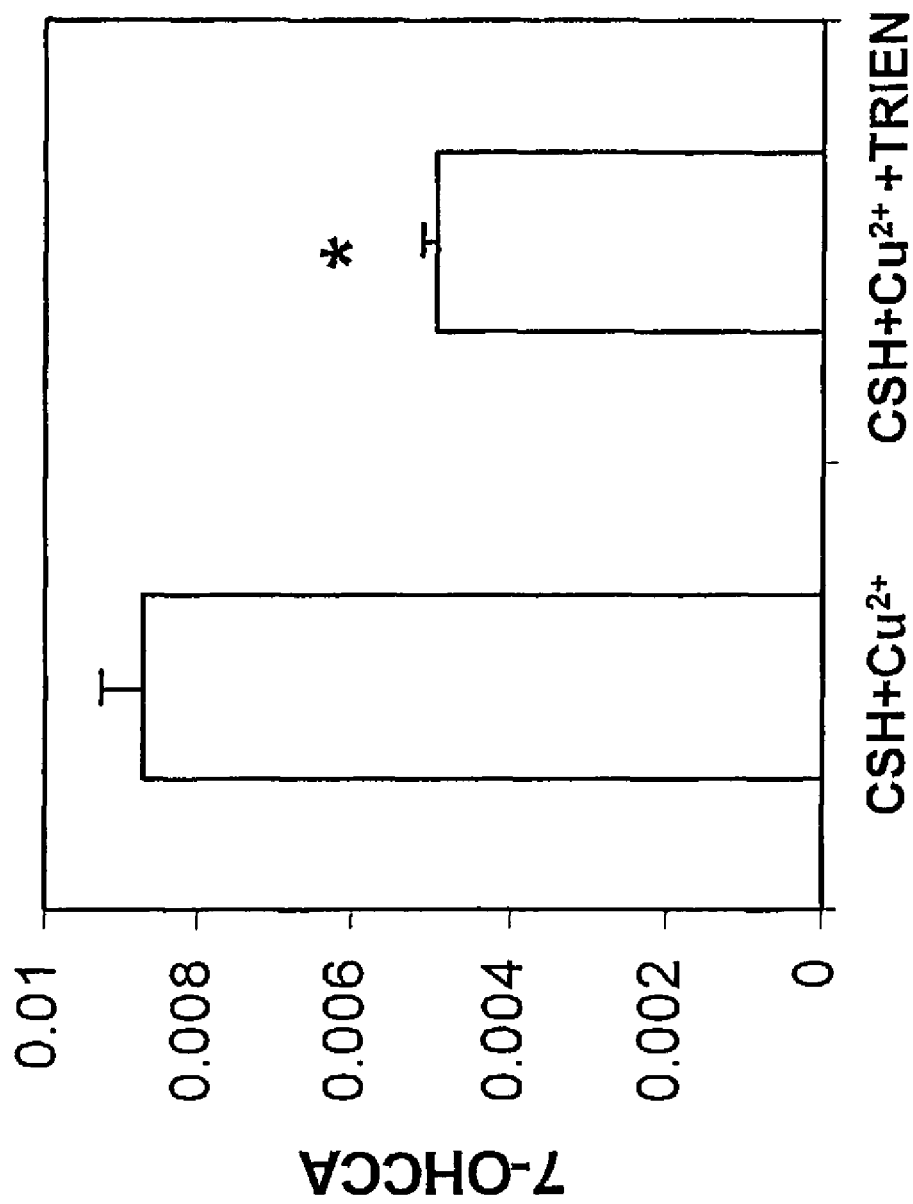
FIG. 1 depicts the effect of copper chelator TRIEN on the generation of hydroxyl radicals (.OH) during $Cu^{2+}$-catalyzed cysteine autoxidation. The reaction mixture included 1 mM TRIEN, 0.2 µM $Cu^{2+}$, 100 µM cysteine, and 1 mM CCA in PBS. The control group contained all components except TRIEN. The reaction condition was pH 7.4 and 37° C. in a humidified atmosphere of 100% air. Fluorescence was measured 4 hr after the reaction began. * Significantly different from the control (p<0.01).

In various aspects, the invention provides methods for treating ocular inflammation, such as methods using copper chelating compounds other than D-penicillamine. Copper chelators may for example be used to treat inflammation which is induced by laser eye therapy or other ocular injuries. In some embodiments, copper chelators may for example be used to treat an eye disease in which a symptom is ocular inflammation, such as allergic conjunctivitis, Reiter's disease, scleritis, iridocyclitis, uveitis, Vogt-Koyanagi syndrome, photophthalmia, nongranulomatous or granulomatous inflammation of uveal tract, necrosis of neoplasms, inflammation produced by foreign particles lodged in the eye, retinal light toxicity (retinal edema from light exposure).

In some embodiments, copper chelators may be used to treat patients who have undergone a laser therapy, such as laser therapy for a condition selected from the group consisting of: macular degeneration, diabetic retinopathy, proliferative diabetic retinopathy, diabetic macular edema, branch retinal vein occlusion, central serous retinopathy, vascular disorders of the fundus (angiomatosis retinae, primary retinal telangiectasis, idiopathic juxtafoveal retinal telangiectasis, acquired retinal macroaneurysms, choroidal hemangioma), retinal breaks, glaucoma (for example following laser iridotomy, argon laser trabeculoplasty, laser cyclophotocoagulation), cataract (for example following yag laser capsulotomy), vitrectomy surgery (for example following endophotocoagulation during surgery), retinal detachment, PVR and choroidal neovascularization (for example following treatment using photocoagulation, photodynamic therapy, or transpupillary thermotherapy). In alternative embodiments, copper chelators may be administered following laser treatments such as of choroidal neovascularization using photocoagulation, photodynamic therapy, or transpupillary thermotherapy.

In some embodiments, preferred copper chelators include the polyamine class of copper chelators, such as TRIEN and TETREN. Alternative ophthalmologically acceptable copper chelators may be synthesised or selected from known compounds and assayed for safety and efficacy in accordance with known methods and methods disclosed herein. Alternative polyamine copper chelators such as diethylenetriaminepentaacetic acid (DTPA) and N,N,N',N-tetrakis(2-pyridylmethyl) ethylenediamine (TPEN) may for example be formulated and adapted for use in accordance with various aspects of the invention. Similarly, copper chelators of other classes, such as 1,4,7,11-tetraazaundecane tetrahydrochloride (TAUD) may be tested for safety and efficacy using known methods and methods disclosed herein, for use in alternative embodiments of the invention. A wide variety of methods may be used to synthesise alternative copper chelators for testing and use in alternative embodiments (as for example disclosed in McMurry et al., Bioconjug Chem 1993 May-June; 4(3):236-45; incorporated herein by reference, including 1,4,7-triazacyclononane, 2-(p-nitrobenzyl)-1,4,7,10-tetraazacy-clododecane, 2-(p-nitrobenzyl)-1,4,8,11-tetraazacyclotetradecane, 2-(p-PhCONH-Bz)-NOTA, 2-(p-nitrobenzyl)-1,4,7,10-tetraazadodecane-1,4,7,10-tetraacetic acid, 2-(p-nitrobenzyl)-1,4,8,11-tetraazatetradecane-1,4,8, 11-tetraacetic acid, and the acyclic ligand 1-(p-nitrobenzyl)-4-methyldiethylenetriamine-N,N,N',N",N"'-pentaacetic acid). In some embodiments, copper chelators may be selected that have an affinity or selectivity for copper binding that is at least as great as the copper affinity or selectivity of TRIEN or TETREN.

I. Biological Activity

The effectiveness of copper chelators in reducing inflammation is illustrated in various ways in the following examples of experimental procedures and Examples 1-3. Example 1 illustrates the effectiveness of the copper chelator TRIEN in inhibiting a copper catalyzed reaction. Example 2 compares the effectiveness of various copper chelators in reducing inflammation resulting from laser eye therapy. Example 3 provides evidence of immune response at the sites of inflammation.

Experimental Procedures

Fluorimetric Assay of Hydroxyl Radicals

Production of OH was estimated using coumarin-3-carboxylic acid (CCA). Nonfluorescent CCA was converted by OH to highly fluorescent 7-hydroxycoumarin-3-carboxylic acid (7-OHCCA). A standard curve was calculated by measuring the fluorescence intensities of a series of concentrations of 7-OHCCA. The OH produced by cysteine auto-oxidation was represented by the corresponding 7-OHCCA concentrations.

Administration of Copper Chelator

Rabbits

The dosage of TRIEN administered was 0.2 mmol/kg·day. TRIEN injection solution was prepared as follows: 438.4 mg of trientine was dissolved in 10 ml distilled $H_2O$ for a final concentration of 200 mM (or 0.2 mmol/ml). The solution was then filtered and stored it at 4° C. The pH of the solution was neutral. The injection volume was 1 ml/kg, according to the above dosage and solution concentration. TRIEN was administered intramuscularly, once a day for one week before laser treatment and 1-3 days after laser treatment. The dosage for TETREN was also 0.2 mmol/kg/day and the administration procedure was the same as for TRIEN.

Rats

The dosage of TRIEN administered was 0.5 mmol/kg·day. TRIEN injection solution was prepared following the same method as described above for rabbits. The solution concentration was 200 mM and the injection volume was 0.25 ml/100 g. TRIEN was administered intraperitoneally, once a day for one week prior to laser treatment, and for 1-3 days after laser treatment. The dosage for TETREN or D-penicillamine was also 0.5 mmol/kg/day and the administration procedure was the same as for TRIEN.

Photodynamic Therapy (PDT) in Rabbits and Photocoagulations in Rats

PDT in Rabbits

Six Pigmented rabbits weighing 1.5-2 kilograms were sedated for all procedures with intramuscular ketamine hydrochloride (50 mg/kg) and xylazine hydrochloride (10 mg/kg). Verteporpin for injection (2 mg/kg) was administered in a bolus by intravenous infusion.

Laser light at 689 nm at a power of 600 mW/cm2 was delivered on a 5 mm spot in one eye from a diode laser (Coherent) using a slit lamp delivery system 15 minutes after verteporfin infusion. Laser light was focused on the outer retina in the posterior pole using a contact lens. After appropriate survival periods, the animals were euthanized using intravenous pentobarbital sodium, and the eyes were enucleated and immediately placed in fixative and processed for histology 24 hours after PDT.

Photocoagulations in Rats

Long-Evans rats weighing 400 g-450 g were used for all procedures with intraperitoneal injection of ketamine hydrochloride (50 mg/kg) and xylazine hydrochloride (10 mg/kg). A glass microscope cover slip was applied to the cornea using gonioscopic solution and the anaesthetized animal placed on the chin rest of a Coherent Argon Dye Laser. Dye laser irradiation at 545 nm wavelength was delivered through a slit lamp. A total of 6 laser spots were placed separately using a setting of 50 um diameter, 0.1 sec duration and 150 mW intensity. The laser spots were positioned between major retinal veins in the right eye only. The animals were sacrificed at 24 hours post photocoagulation treatment. The enucleated eyes were immediately placed in fixative and processed for histology.

Histological Evaluation of Inflammation

The eyes were fixed with 4% paraformaldehide for 24 hours and the cornea, lens, and vitreous were removed. Eye cup photographs were taken under a microscope. The tissues were placed in freezing compound and frozen with liquid nitrogen. Cross sections (6-8 um) were cut from each specimen. The sections were stained with hematoxylin and eosin for measurement of retinal thickness and also were stained for the presence of macrophages with ED-1, a marker for macrophage cells, using immunohistochemistry techniques and examined with microscope.

EXAMPLE 1

Inhibition of Copper-Catalyzed Generation of Hydroxyl Radicals by Copper Chelator TRIEN In order to show that copper is the major catalyst in the auto-oxidation reaction and in the generation of free radicals a copper chelator was used to inhibit the generation of free radicals. The copper chelator used was TRIEN, which is used clinically for the treatment of Wilson's disease. The effect of TRIEN on the generation of .OH from cysteine autoxidation was tested by measuring the production of .OH with a CCA fluorescence assay. The reaction mixture included 1 mM, TRIEN, 100 μM cysteine, 0.2 μM $Cu^{2+}$, 1 mM CCA, and PBS. The control contains all components except TRIEN. As shown in FIG. 1, the addition of TRIEN inhibited the generation of .OH from copper-catalyzed cysteine auto-oxidation.

EXAMPLE 2

Effect of Copper Chelators on the Inflammatory Reaction Following PDT and Photocoagulations To determine the effect of copper chelators on the inflammatory reaction after PDT and photocoagulation, retinal thickness was measured following laser therapy.

Retinal Thickness (Edema) after Laser Therapy

Figure 2:
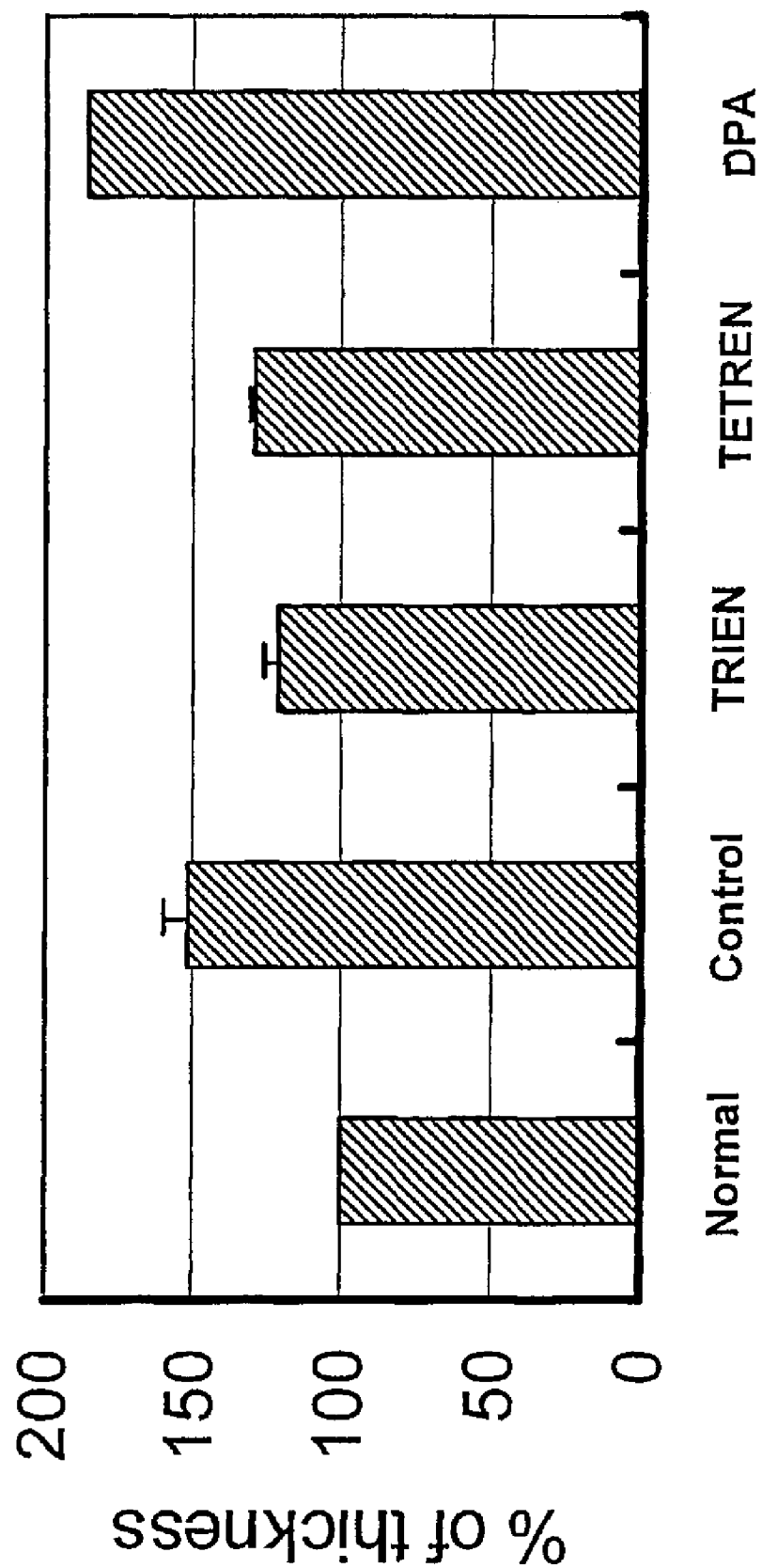
FIG. 2 depicts the retinal thickness (edema) at day 1 post laser treatment (photocoagulation) in rats. The retinal thickness was measured from eyes of rats treated with TRIEN or TETREN or D-PA, and compared to the retinal thickness from eyes of rats injected with saline (controls) and to normal retina (no laser treatment and no drug/saline injections). Coherent Argon Dye Laser irradiation at 545 nm wavelength was delivered through a slit lamp. A total of 6 laser spots were placed separately using a setting of 50 um diameter, 0.1 sec duration and 150 mW intensity. The retinal thickness of eyes from control animals (saline injected) is greater than that of normal (no laser treatment, no drug/saline injections) retina and eyes from animals treated with TRIEN or TETREN. The retinal thickness of eyes from animals injected with D-PA is greater than that in control eyes.

A comparison was made of rat eyes following photocoagulation therapy, where the rats received either TRIEN, TETREN, D-PA or no copper chelator (control treated) prior to laser therapy. When the rat eyes were compared on the basis of retinal thickness, the eyes from control animals (saline injected) were greater than those of the TRIEN or TETREN groups as represented in FIG. 2. At twenty-four hours post photocoagulation treatment, the retinal thickness of eyes from control animals was 50% greater than that in normal retina, where no laser treatment and no copper chelator was given. The retinal thickness of eyes of TRIEN injected animals was 23% greater than that in normal retina and the retinal thickness of eyes from TETREN-treated animals was 26% greater than that in normal retina. However, when the retinal thickness of eyes from D-PA treated animals was measure they were found to be 85% greater than that of normal retinal thickness and 35% greater than that in the control animals.

Figure 3:
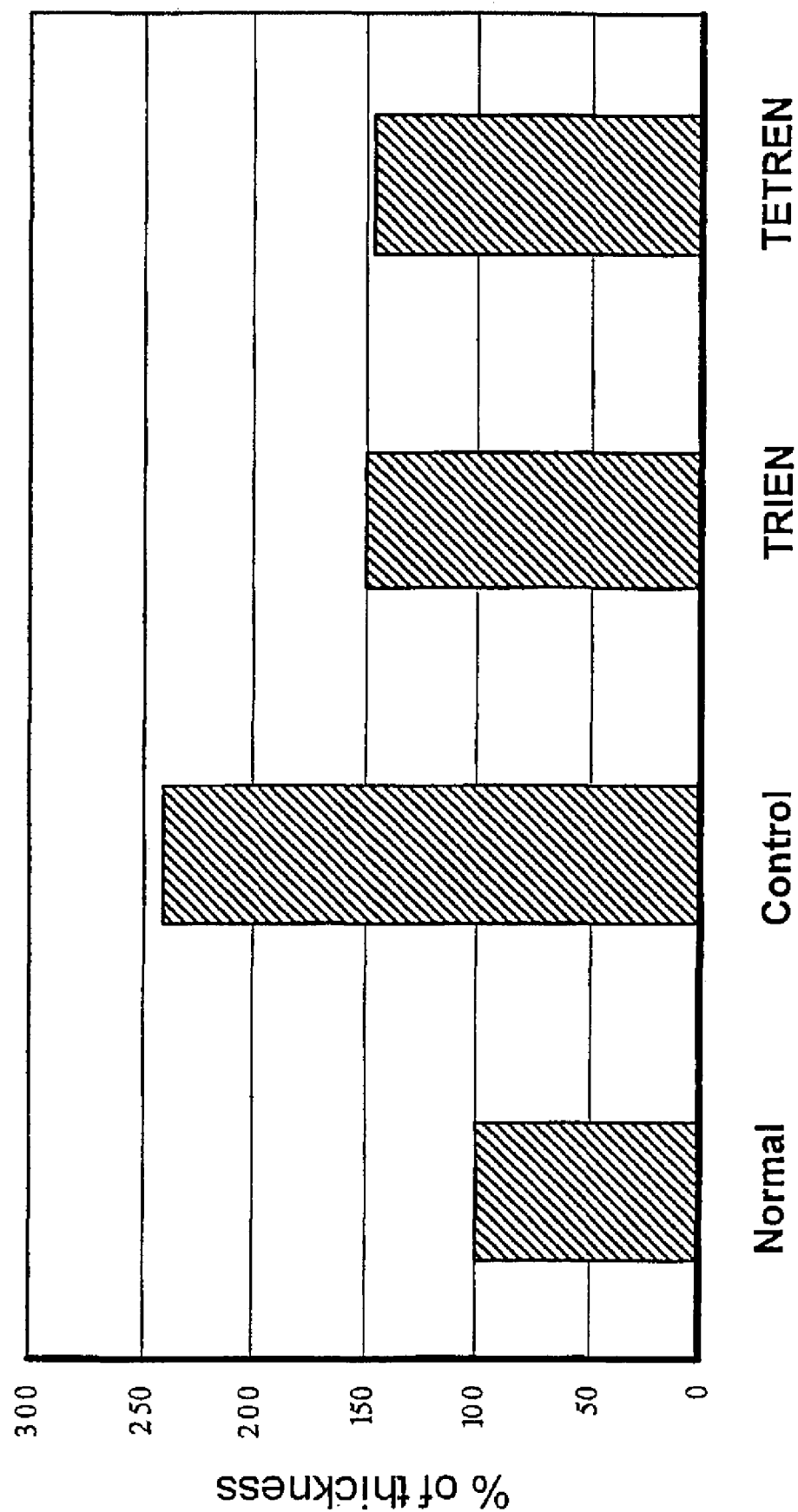
FIG. 3 depicts the retinal thickness (edema) at day 1 post PDT in rabbits. The graph shows retinal edema at 1 day post PDT from animals treated with TRIEN or TETREN (0.2 mM/day), or from control animals (saline injected). Laser light at 689 nm at a power of 600 mW/cm2 was delivered on a 5 mm spot in one eye from a diode laser (Coherent) using a slit lamp delivery system 15 minutes after verteporfin infusion. The retinal thickness from animals treated with TRIEN and TETREN is significantly less than that in control (saline injected) animals.

A comparison was also made of rabbit eyes following PDT, where the rabbits received either TRIEN, TETREN or no copper chelator (control treated) prior to laser therapy. When the rabbit eyes were compared on the basis of retinal thickness, the eyes from control treated animals(saline injected) were greater than that eyes from animals treated with TRIEN or TETREN or untreated eyes, as shown in FIG. 3. Twenty-four hours after PDT treatment, the retinal thickness of eyes from control animals (saline injected) was 140% greater than that in normal retina; the retinal thickness of TRIEN treated eyes was 50% greater than that in normal retina; the retinal thickness of TETREN treated eyes was 45% greater than that in normal retina.

The results show that the copper chelators TRIEN or TETREN were effective in reducing inflammation resulting from laser eye therapy, while DPA showed the opposite effect in rats.

EXAMPLE 3

Immunohistochemical Examinations after Laser Treatment

Figure 4:
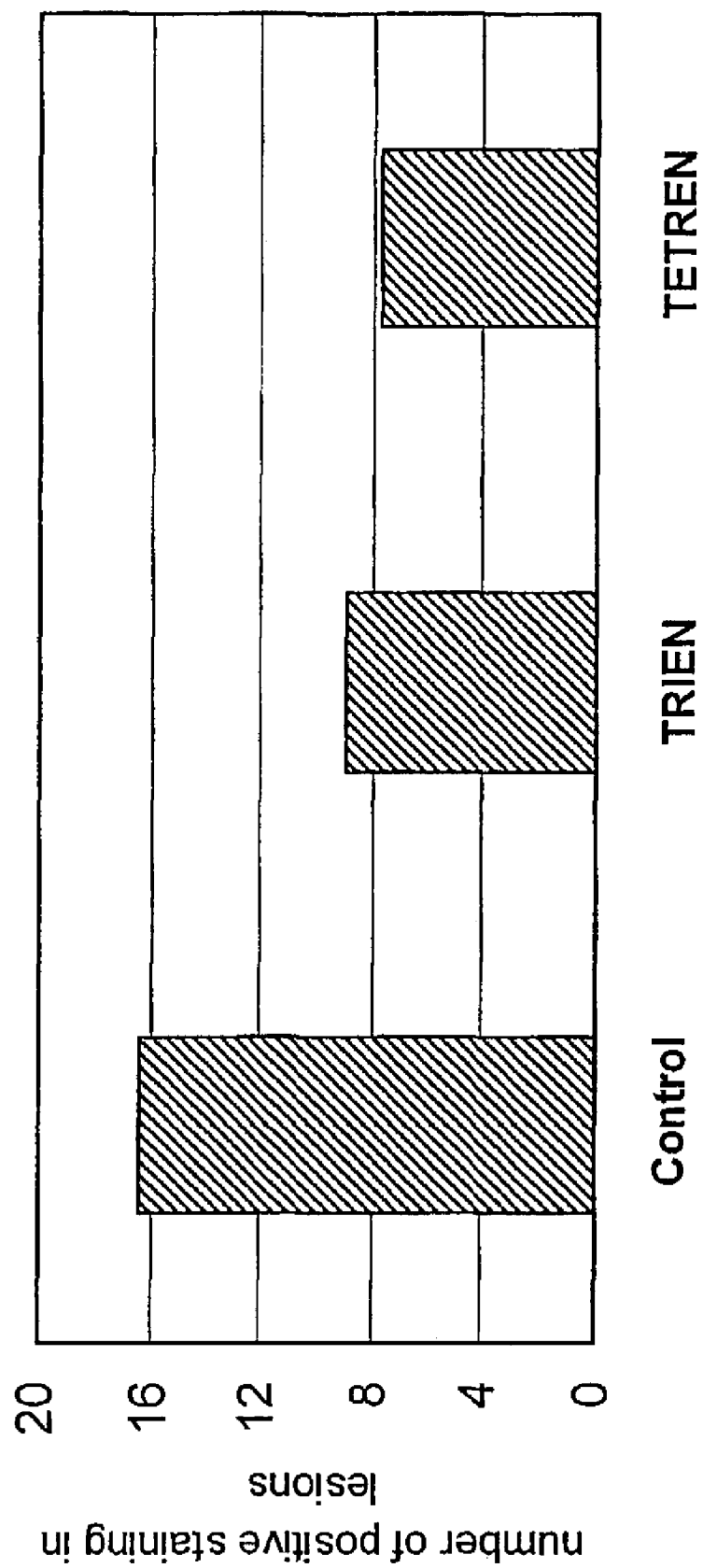
FIG. 4 depicts the ED-1 immunostaining of retina at Day 1 post photocoagulation treatment in rats. The graph, illustrates the number of ED-1 immunoreactive cells. ED-1 is a marker for macrophage cells. Coherent Argon Dye Laser irradiation at 545 nm wavelength was delivered through a slit lamp using a setting of 50 um diameter, 0.1 sec duration and 150 mW intensity. The lesions were quantified by counting the number of positive cells in an average of four 40× objective fields. The numbers of ED-1 positive cells are less in retina of TRIEN or TETREN treated animals compared to control (saline injected) animals. The numbers of ED-1 positive cells of Trientine-treated eyes were two times less than of control. The numbers of ED-1 positive cells of TETREN treated eyes were 2.5 times less than that of controls animals.

To determine if the tissue inflammation could be correlated with the immune response were stained with macrophage antibody (ED-1). TRIEN and TETREN inhibited the immunoresponse in ocular tissues following laser therapy. All experimental animals showed a similar sequence of immunohistochemical findings, which are summarized in FIG. 4. At twenty-four hours after laser treatment, the macrophage staining was clearly evident in eyes from control animals (saline injected). In eyes from TRIEN and TETREN treated animals showed fewer macrophages at the laser therapy sites. The number of ED-1 positive retina cells in TRIEN treated animals were approximately half that of the controls (saline injected). And similarly the number of ED-1 positive retina cells in TETREN treated animals were more than half that of control animals.

These results indicate that the copper chelators TRIEN or TETREN were effective in reducing immune response by macrophages following laser eye therapy.

II. Pharmaceutical Preparations and Treatments

Humans, and other animals, in particular, mammals, suffering from ocular inflammation due to laser therapy or other eye injury may be treated by administering to the patient an effective amount of one or more of the above-identified copper chelators or a pharmaceutically acceptable derivative or salt thereof in a pharmaceutically acceptable carrier or diluent. The active materials can be administered by any appropriate route, for example, orally, parenterally, intravenously, intradermally, or subcutaneously.

As used herein, the term pharmaceutically acceptable salts or complexes refers to salts or complexes that retain the desired biological activity of the above-identified compounds and exhibit minimal undesired toxicological effects. Non-limiting examples of such salts are acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. For example, triethylene tetramine tetrahydrochloride or trientine hydrochloride (which may for example be available as 250 mg capsules from Merck & Co. Inc. of New Jersey, U.S.A. under the trademark SYPRINE).

The active compound may be included in the pharmaceutically acceptable carrier or diluent in an amount sufficient to deliver to a patient a therapeutically effective amount without causing serious toxic effects in the patient treated. In some embodiments, a preferred dose of the active compound for all of the above-mentioned conditions is in the range from about 0.5 to 500 mg/kg, preferably 1 to 100 mg/kg per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art. For example, trientine hydrochloride may be administered in an initial does of 500-750 mg/day for pediatric patients and 750-1250 mg/day for adults, given in divided doses two, three or four times daily. Such doses may be increased to 2000 mg/day for adults or 1500 mg/day for pediatric patients (aged 12 or under), when clinical response to an initial dose is not adequate. Oral medications may for example be taken on an empty stomach, at least one hour before meals or two hours after meals and at least one hour apart form any other drug or food.

An effective amount of a compound of the invention may include a therapeutically effective amount or a prophylactically effective amount of the compound. A "therapeutically effective amount" generally refers to an amount effective, at dosages and for periods of time necessary, to achieve the desired therapeutic result, such as reduction or reversal of ocular inflammation. A therapeutically effective amount of copper chelator may vary according to factors such as the disease state, age, sex, and weight of the individual, and the ability of the copper chelator to elicit a desired response in the individual. Dosage regimens may be adjusted to provide the optimum therapeutic response. A therapeutically effective amount is also one in which any toxic or detrimental effects of the SS ligand are outweighed by the therapeutically beneficial effects. A "prophylactically effective amount" refers to an amount effective, at dosages and for periods of time necessary, to achieve the desired prophylactic result, such as preventing or inhibiting the rate of ocular inflammation. A prophylactically effective amount can be determined as described above for the therapeutically effective amount. Copper chelators may for example be administered in a prophylactically effective amount prior to laser eye therapy, or prior to other procedures or treatments that are likely to induce ocular inflammation. Typically, since a prophylactic dose is used in subjects prior to or at an earlier stage of disease, the prophylactically effective amount will be less than the therapeutically effective amount.

The compounds of the invention may be administered in any suitable unit dosage form, including but not limited to one containing 1 to 3000 mg, preferably 5 to 500 mg of active ingredient per unit dosage form. An oral dosage of 25-250 mg may for example be convenient.

In some embodiments, the active ingredient may for example be administered to achieve peak plasma concentrations of the active compound of about 0.1 to 100 µM, or about 1-10 µM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set-forth herein are exemplary only and are not intended to limit the scope or practice of the claimed composition. The active ingredient may be administered at once, or may be divided into a number of smaller doses to be administered at varying intervals of time.

Solutions or suspensions used for parenteral, intradermal, subcutaneous, or topical application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

If administered intravenously, preferred carriers are physiological saline or phosphate buffered saline (PBS). The active compound can also be administered through a transdermal patch. Methods for preparing transdermal patches are known to those skilled in the art. For example, see Brown L., and Langer R., Transdermal Delivery of Drugs, Annual Review of Medicine, 39:221-229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

Liposomal suspensions may also be pharmaceutically acceptable carriers. These may be prepared according to methods known to those skilled in the art, for example, as described in U.S. Pat. No. 4,522,811. For example, liposome formulations may be prepared by dissolving appropriate lipid (s) (such as stearoyl phosphatidyl ethanolamine stearoyl phosphatidyl choline, arachadoyl phosphatidy choline, and cholesterol) in an inorganic solvent that is then evaporated, leaving behind a thin film of dried lipid on the surface of the container. An aqueous solution of the active compound or its monophosphate, and/or triphosphate derivatives are then introduced into the container. The container is then swirled by hand to free the lipid aggregates, thereby forming the liposomal suspension.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

In alternative embodiments, the active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors. A further form of administration of copper chelators in various aspects of the invention is to the eye. A copper chelator may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye. In some embodiments, anti-inflammatory treatment with copper chelators may be undertaken following photodynamic therapy (such as is described in U.S. Pat. No. 5,798,349 issued 25 Aug. 1998, incorporated herein by reference).

The active compound or pharmaceutically acceptable derivatives or salts thereof can also be administered with other active materials that do not impair the desired action, or with materials that supplement the desired action, such as antibiotics, antifungals, antiinflammatories, or antiviral compounds. The active compounds can be administered with lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and (3-blockers such as propanalol, terbutalol, and labetalol. The compounds can also be administered in combination with nonsteroidal antiinflammatories such as ibuprofen, indomethacin, aspirin, fenoprofen, mefenamic acid, flufenamic acid, sulindac. The compounds may also be administered with ophthalmologically acceptable formulations of corticosteriods.

In accordance with various aspects of the invention, copper chelators may be formulated as ophthalmologicals. In some embodiments, the invention accordingly provides pharmaceutical compositions adapted for administration to the eye comprising a copper chelator in an ophthalmologically acceptable carrier. For example, copper chelators may be included in conventional irrigation solutions or viscoelastic solutions used during ocular surgery, or lens implants may be coated or impregnated with copper chelators.

Pharmaceutical compositions of the invention may contain therapeutic agents other than copper chelators, such as other nonsteroidal ophthalmic anti-inflammatory agents, including agents selected from the group consisting of: diclofenac sodium, flurbiprofen sodium, indomethacin, and ketorolac tromethamine. Ophthalmologicals of the invention may include ophthalmic local anesthetics, such as benoxinate, proparacaine hydrochloridde or tetracaine hydrochloride. Ophthalmologicals of the invention may also include compounds used to formulate artificial tears, such as carbodymethylcellulose sodium, dextran 70/hydroxypropyl methylcellulose, glycerin, hydroxypropyl cellulose, hydroxypropyl methylcellulose, methylcellulose, polysorbate 80, polyvinyl alcohol or sodium hyaluronate. Ophthalmologically acceptable analgesics may also be formulated with copper chelators to provide ophthalmologicals of the invention.

In some embodiments, ophthalmological formulations of the invention may for example contain about 0.1% to 15% by weight of copper chelating medicament, such as about 0.5% to 4% by weight of medicament, the remainder being comprised of carriers and other excipients known in the art for ophthalmological preparations. In some embodiments, the invention provides for treatment of ocular inflammation by topical ocular administration of copper chelators. In accordance with various aspects of the invention, copper chelators may be formulated as ophthalmologically acceptable salts of copper chelating compounds.

Individuals being treated with copper chelators in accordance with various aspects of the invention to reduce ocular copper levels, may also limit the consumption of any supplemental dietary copper, which may have an adverse effect on the drug's performance.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

The examples herein are illustrative of various aspects of the invention, and are not limiting of the broad aspects of the invention as disclosed and claimed.

What is claimed is:

1. A method for treating ocular inflammation in an animal in need of such treatment comprising systemically administering to the animal an effective amount of a polyamine copper chelator having from 4 to 6 amine groups.

2. The method according to claim 1, wherein the animal is a mammal.

3. The method according to claim 1, wherein the animal is a human.

4. The method according to claim 3, wherein the ocular inflammation results from laser eye therapy.

5. The method according to claim 3, wherein the ocular inflammation results from trauma.

6. The method according to claim 3, wherein the ocular inflammation results from exposure to ultraviolet light.

7. The method according to claim 3, wherein the ocular inflammation results from exposure to chemical stimuli.

8. The method according to claim 3, wherein the ocular inflammation results from exposure to a toxin.

9. The method according to claim 3, wherein the ocular inflammation results from a condition selected from the group consisting of allergic conjunctivitis, Reiter's disease, scleritis, iridocyclitis, uveitis, Vogt-Koyanagi syndrome, photophthalmia, nongranulomatous inflammation of the uveal tract, granulomatous inflammation of the uveal tract, necrosis of neoplasms, foreign particles lodged in the eye, retinal light toxicity and retinal edema from light exposure.

10. The method according to claim 4, wherein the copper chelator is triethylenetetramine.

11. The method according to claim 5, wherein the copper chelator is triethylenetetramine.

12. The method according to claim 6, wherein the copper chelator is triethylenetetramine.

13. The method according to claim 7, wherein the copper chelator is triethylenetetramine.

14. The method according to claim 8, wherein the copper chelator is triethylenetetramine.

15. The method according to claim 9, wherein the copper chelator is triethylenetetramine.

16. The method according to claim 4, wherein the copper chelator is tetraethylenepentamine.

17. The method according to claim 5, wherein the copper chelator is tetraethylenepentamine.

18. The method according to claim 6, wherein the copper chelator is tetraethylenepentamine.

19. The method according to claim 7, wherein the copper chelator is tetraethylenepentamine.

20. The method according to claim 8, wherein the copper chelator is tetraethylenepentamine.

21. The method according to claim 9, wherein the copper chelator is tetraethylenepentamine.

22. The method according to claim 3, wherein the systemically administering is oral.

23. The method according to claim 3, wherein the systemically administering is parenterally.

24. The method according to claim 3, wherein the polyamine copper chelator having at least 4 amine groups does not have more than 5 amine groups.

25. The method according to claim 24, wherein the ocular inflammation results from at least one of the group consisting of: laser eye therapy, trauma, exposure to ultraviolet light, exposure to chemical stimuli, and exposure to a toxin.

26. The method according to claim 24, wherein the ocular inflammation results from a condition selected from the group consisting of allergic conjunctivitis, Reiter's disease, scleritis, iridocyclitis, uveitis, Vogt-Koyanagi syndrome, photophthalmia, nongranulomatous inflammation of the uveal tract; granulomatous inflammation of the uveal tract, necrosis of neoplasms, foreign particles lodged in the eye, retinal light toxicity and retinal edema from light exposure.

27. The method according to claim 24, wherein the systemically administering is selected from the group consisting of: oral and parenterally.

* * * * *